United States Patent [19]
Cummings et al.

[11] Patent Number: 5,932,800
[45] Date of Patent: Aug. 3, 1999

[54] VISCOSITY TESTING DEVICE

[75] Inventors: Michael W. Cummings; Wayne T. Nowlin, both of Murfreesboro, Tenn.

[73] Assignee: Nissan Motor Manufacturing Corp., Smyrna, Tenn.

[21] Appl. No.: 09/042,902

[22] Filed: Mar. 17, 1998

[51] Int. Cl.[6] .................................................. G01N 11/04
[52] U.S. Cl. ...................... 73/54.14; 73/54.1; 73/54.04
[58] Field of Search ................................ 73/54.04, 54.11, 73/54.14

[56] References Cited

U.S. PATENT DOCUMENTS 2,526,832  10/1950  Smith ..................................... 73/54.11
5,388,447  2/1995  Fitch et al. ............................. 73/54.14

Primary Examiner—Michael Brock
Assistant Examiner—Chad Soliz
Attorney, Agent, or Firm—J. C. Waddey, Jr.; Waddey & Patterson

[57] ABSTRACT

A device for testing the viscosity of a fluid contained in a cartridge comprising a tubular housing, a pair of end caps, one end cap being configured for operable connection to a piston and cylinder assembly, and the other end cap being configured to receive an adapter that is connectable to the cartridge and to a plug having an orifice of a predetermined diameter through which the fluid in the cartridge may be extruded.

9 Claims, 3 Drawing Sheets

5,932,800

VISCOSITY TESTING DEVICE

BACKGROUND OF THE INVENTION

The present invention relates generally to devices for measuring the viscosity of a fluid, and more particularly to a device for testing a fluid sample contained in a cylindrical tube.

Fluids used in processing or manufacturing are often packaged and shipped in bulk. Cartridges containing small batch samples useful for quality control testing may be provided along with the bulk material. For example, a supplier of liquid urethane, which is typically purchased in fifty gallon drums, may also provide a cartridge containing a sample of the batch material contained in the drum.

Heretofore, the material contained in the cartridge was placed in a pressure flow viscometer cup for testing. One drawback associated with this procedure is that it requires the direct handling of the sample material and exposes the material to air and other elements during testing. The exposure of the sample to air causes the partial curing and contamination of the material, which can affect test results.

Furthermore, the devices for testing viscosity typically employ a "floating" piston, which extrudes the sample through an orifice of known diameter under a given pressure. The output is weighed and the viscosity of the material is determined. Because currently available devices involve the handling of the material during testing, meticulous cleaning of the equipment is required to maintain consistency in testing.

It will be appreciated by those skilled in the art that it is desirable to have a device for testing the viscosity of a the fluid in a container. To this end, there have been several attempts to devise such devices.

One such attempt was disclosed in U.S. Pat. No. 2,426,393, issued to Fischer, which is incorporated by reference as if fully set forth herein. The Fischer device is directed to an inline viscometer for determining the viscosity of a fluid in motion. The device comprises a rotameter tube wherein are disposed two separate metering floats. One float is insensitive to, and unaffected by, variations in viscosity so that its position is determined solely by the rate of flow of the fluid. The other float is sensitive to, and affected by, variations in both viscosity and rate of flow. Accordingly, the viscosity of the flowing fluid may be determined by the difference in the positions of the two metering floats and the variations in the fluid viscosity can be determined by the corresponding variations and the difference of the position of the two floats.

U.S. Pat. No. 5,388,447, issued to Fitch, et al., is directed to a viscosity measurement apparatus for measuring viscosity of a fluid under known pressure. A fluid sample passes through a tube of known diameter and length. A piston, sealably engaged with a closed chamber, which is in fluid communication with the tube, may be moved by force of the fluid passing through the tube. A linear gage measures the time required to move the piston. A mechanism is provided to reset the piston by forcing fluid back through the tube to empty the chamber to begin another measurement. The device may be attached to a sampling valve of a fluid system under pressure.

Japanese Patent No. 58/21542, issued to Yamada, is directed to a flow testing device comprising a cylinder having a nozzle at its lower end and a plunger positioned within the cylinder for extruding the fluid sample through the nozzle.

Further, the list that follows includes patents directed to other viscosity measuring devices.

| Patent No. | Inventor |
|---|---|
| 1,989,050 | Albersheim, et al |
| 2,011,862 | Konheim, et al |
| 3,195,351 | Feldman |

While the patents referenced hereinabove generally disclose devices for testing the viscosity of a fluid, none discloses a viscometer configured to enable direct testing of a fluid contained in a cartridge. What is needed then, is a viscometer that enables the testing of the fluid contained in a cartridge without requiring that the sample be handled or transferred to a testing device, thereby exposing the sample to air, which affects the consistency of the fluid and exposes the sample to airborne contaminants.

SUMMARY OF THE INVENTION

The present invention is directed to a viscosity testing device comprising a tubular housing configured to receive a cartridge containing a sample of fluid to be tested. End caps are provided to capture the cartridge within the housing. Accordingly, the proximal end of the housing is capped with a threaded cap which includes a threaded nipple for enabling attachment to a piston and cylinder assembly. A central bore configured to receive a positive displacement piston or ram extends through the end cap and nipple. Thus, the ram may extends through the bore into direct engagement with an end of the cartridge. The distal end of the housing is capped with a threaded cap having a central bore for receiving an adapter or sleeve. One end of the adapter or sleeve is configured for attachment to the cartridge, and the other end is configured to receive a plug having an orifice of known diameter.

The viscosity testing holder of the present invention eliminates the need for having to remove the material from the cartridge, place it in a cup and then test it. The testing is done directly from the cartridge, thereby avoiding a messy clean up and further avoiding exposure of the contents of the cartridge of the elements until after the test is completed.

It is an object of the present invention to provide a viscometer for testing a fluid sample contained within a cartridge.

It is an object of the present invention to provide a viscometer for enabling the testing of a fluid contained in a cartridge without removing the fluid from the cartridge.

These and other objects, features and advantages shall become apparent after consideration of the description and drawings set forth herein. All such objects, features and advantages are contemplated to be within the scope of the present invention even though not specifically set forth herein.

DESCRIPTION OF THE PREFERRED EMBODIMENT

Figure 1:
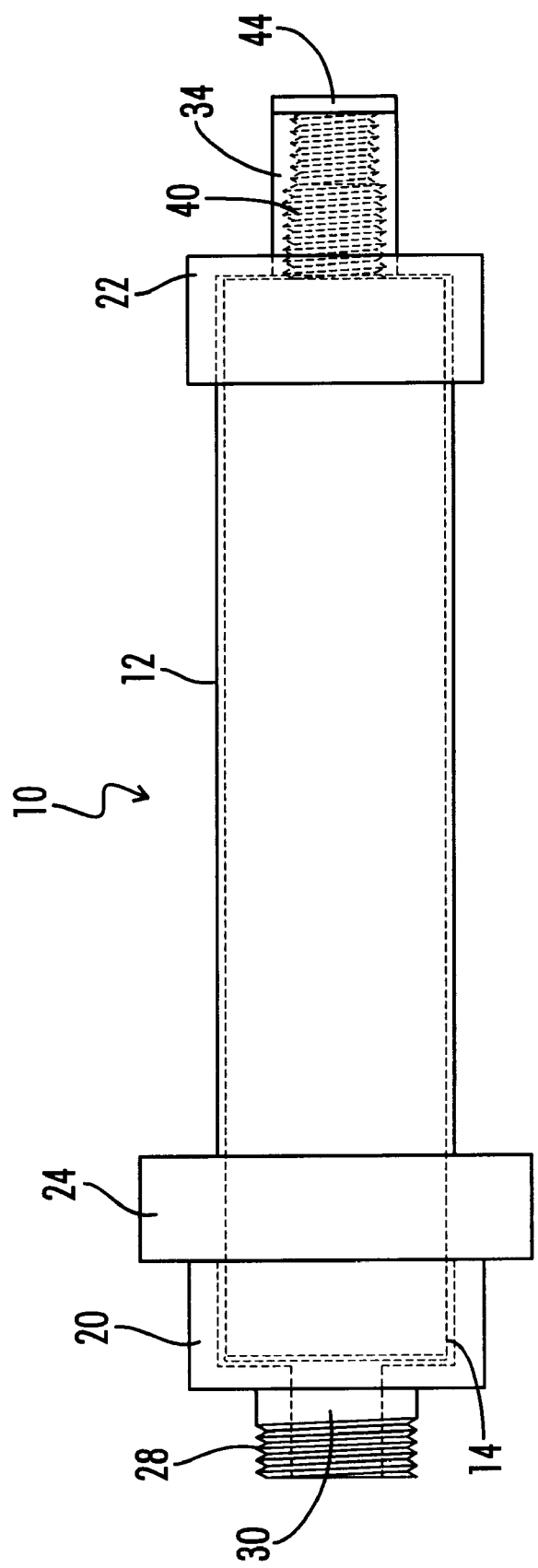
FIG. 1 is a side view of the viscometer of the present invention shown in operable engagement with a cartridge containing fluid.

An embodiment of the viscometer of the present invention is designated generally by reference numeral 10 in FIG. 1.

Viscometer 10 comprises a tubular housing 12 configured to receive a cartridge 14 containing a fluid. The housing 12 is preferably constructed of aluminum, but may be constructed of any other suitable material, including without limitation metals, plastics, composites, synthetics and the like.

Figure 2:
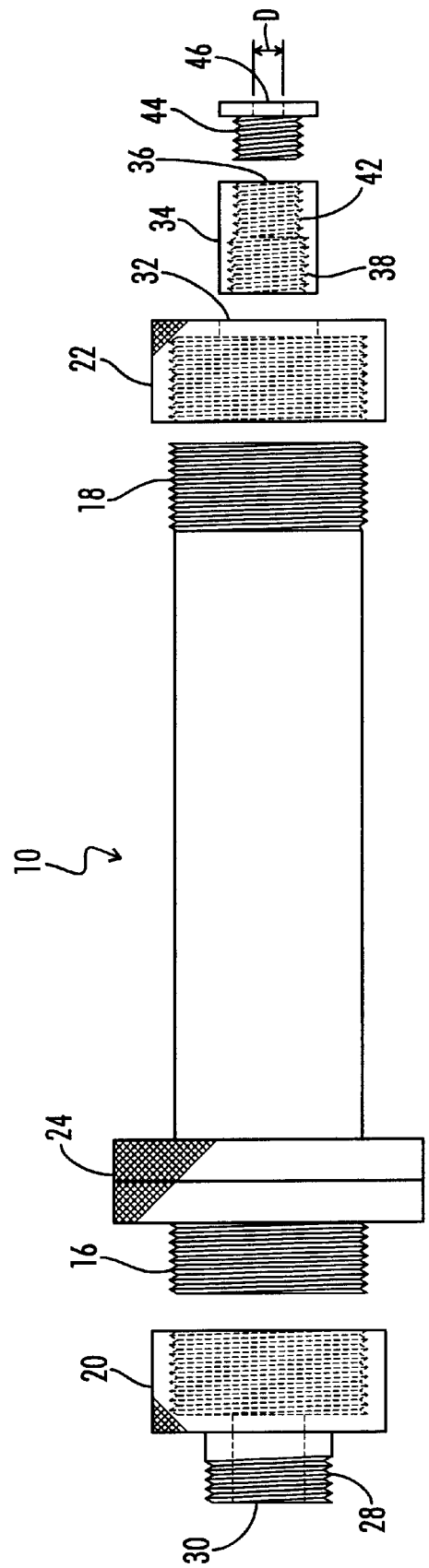
FIG. 2 is an exploded view of the viscometer of the present invention.

The housing 12 includes proximal and distal ends 16 and 18 (see FIG. 2), which are preferably threaded to receive cooperatively threaded end caps 20 and 22. The threaded ends 16 and 18 and end caps 20 and 22 enable any adjustments necessary as a result of inconsistent cartridge 14 length. However, it is also contemplated that the end caps 20 and 22 be secured to the ends 16 and 18 of the housing 12 by fasteners or any other suitable means of adjustable attachment. A grip ring 24 may be provided adjacent the proximal end 16 of the housing 12. The end caps 20 and 22 and the grip ring 24 may have a knurled outer surface.

Figure 3:
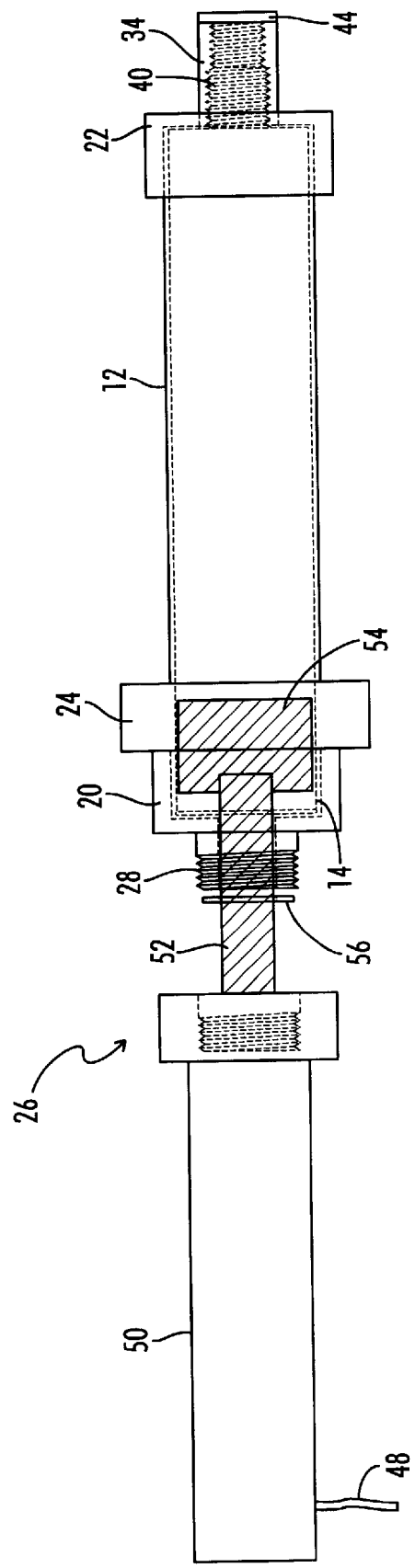
FIG. 3 is a perspective view of the viscometer of the present invention shown in operable engagement with a piston and cylinder assembly.

End cap 20, which is attachable to the proximal end 16 of the housing 12, is configured for operable attachment to a piston and cylinder assembly 26, as shown in FIG. 3. Accordingly, end cap 20 includes a threaded nipple 28 protruding therefrom for attachment to a cooperatively threaded female connection on the piston and cylinder assembly 26. A central bore 30 extends through nipple 28 and end cap 20. End cap 22, which is attachable to the distal end 18 of the housing 12, includes a central bore 32 configured to receive an adapter or sleeve 34.

The adapter or sleeve 34 includes a central bore 36, one end 38 of which is configured for operable attachment to an end of the cartridge 14. Typically, the cartridge 14 includes an externally threaded nozzle 40 at one end. Accordingly, end 38 of the adapter 34 is internally threaded to mate with the nozzle 40. The other end 42 of the adapter 34 is configured to receive a threaded plug 44 having an orifice 46 of a predetermined diameter D.

The piston and cylinder assembly 26 includes a regulated air supply 48 operably attached to an air cylinder 50, and a positive displacement piston or ram 52 for exerting a force on an end of the cartridge 14 contained within the housing 12. A plate 54 for engaging the end of the cartridge is threadably attached to the end of the piston 52. In the preferred embodiment, the plate 54 is circular and sized to engage the entire end of the cartridge 14 so that the force from the piston 52 is uniformly distributed across the entire end surface of the cartridge 14.

MODE OF OPERATION

To use the viscometer 10 of the present invention, a cartridge 14 containing a fluid to be tested is inserted into the housing 12 and end cap 22 is attached to the housing 12. Plate 54 is inserted into end 16 of the housing 12 to engage the end of the cartridge 14, and end cap 20 is threaded onto the housing 12. The plug 44 is attached to the adapter 34, and the adapter 34 is, in turn, threadably attached to the nozzle 40 of the cartridge 14.

The viscometer 10 is then operably attached to the piston and cylinder assembly 26. Accordingly, the end of the piston 52 is threaded onto the plate 54, and the nipple 28 on end cap 20 is threadably attached to the air cylinder 50. A gasket 56 is inserted between the nipple 28 and the threaded connection on the air cylinder 50 to achieve a tight air seal.

Air from the regulated air supply 48 fills the air cylinder 50 and causes the piston 52 and the plate 54 to exert a force on the end of the cartridge 14. The force on the end of the cartridge 14 causes the fluid contained therein to pass through the orifice 46 in plug 44. The viscosity of the fluid may be determined from the rate the fluid extrudes from the orifice 46.

Accordingly, the viscometer 10 of the present invention enables viscosity testing of the fluid directly from the cartridge 14 and, thus, eliminates handling of the fluid sample by testing personnel and contamination of the sample resulting from exposure to airborne elements.

Thus, although there have been described particular embodiments of the present invention of a new and useful viscosity testing device, it is not intended that such references be construed as limitations upon the scope of this invention except as set forth in the following claims. Further, any dimensions used in the preferred embodiment are not intended to be construed as limitations upon the scope of this invention except as set forth in the following claims.

What I claim is:

1. A device for testing the viscosity of a fluid contained in a cartridge, comprising:

a housing including a first end and a second end spaced from said first end a distance approximately the length of the cartridge to be tested and configured to receive the cartridge;

an adapter having a first end configured for attachment to the cartridge and a second end configured to receive a plug having an orifice of a predetermined diameter;

end caps configured to cooperatively engage the ends of the housing, one end cap being configured to receive the adapter and the other end cap being configured for operable attachment to a cylinder and piston assembly such that the fluid contained in the cartridge is forced through the orifice in response to a force applied to the cartridge by the piston.

2. The device of claim 1, further comprising:

a grip ring positioned intermediate the ends of the housing.

3. The device of claim 1, wherein the outer peripheral surface of each of the end caps is knurled.

4. The device of claim 1, wherein the first end of the adapter is internally threaded to cooperatively receive a threaded nozzle on an end of the cartridge, and the second end of the adapter includes means for attaching the second end of said adapter to said plug.

5. The device of claim 1, wherein the ends of the housing and the end caps are cooperatively threaded.

6. The device of claim 1, wherein the configuration of the said other end cap includes a nipple and said nipple is threaded to cooperatively engage the cylinder and piston assembly.

7. A device for testing the viscosity of a fluid contained in a cartridge, comprising:

a tubular housing having opposing ends, each end being threaded;

an adapter having a first end configured to cooperatively receive an end of the cartridge from which the fluid is dispensed, and a second end configured to cooperatively receive a plug having an orifice of a predetermined diameter through which the fluid is extruded;

end caps cooperatively threaded to mate with and attach to respective opposing end of said tubular housing,
      one end cap having a nipple configured for operable attachment to a cylinder and piston assembly, the cap and nipple having a central bore configured to receive the piston,
      and the other end cap having a bore for receiving the adapter.

8. The device of claim 7, wherein the device is constructed of aluminum.

9. A method for testing the viscosity of a fluid contained in a cartridge, comprising the steps of:

(a) providing a housing for the cartridge, the housing having a first end configured for operable connection to a cylinder and piston assembly, and a second end configured to enable operable connection of the cartridge to a plug having an orifice of a predetermined diameter;

(b) applying a constant known force to the piston to force the fluid contained within the cartridge through the orifice;

(c) measuring the weight of the fluid passing through the orifice over a predetermined period of time; and (d) calculating the viscosity of the fluid using the known information and the information determined in performing step (c) above.

* * * * *